(12) United States Patent
Herencia et al.

(10) Patent No.: US 8,337,590 B2
(45) Date of Patent: Dec. 25, 2012

(54) DEVICE FOR DRYING A GAS, IN PARTICULAR AIR, APPLICATION THEREOF TO A DEVICE, AND METHOD FOR COLLECTING A GAS SAMPLE

(75) Inventors: Ignacio Valor Herencia, Alicante (ES); Juan Manuel Juarez Galan, Alicante (ES)

(73) Assignee: R + I Alliance, Paris (FR)

( * ) Notice: Subject to any disclaimer, the term of this patent is extended or adjusted under 35 U.S.C. 154(b) by 274 days.

(21) Appl. No.: 12/866,514

(22) PCT Filed: Feb. 4, 2009

(86) PCT No.: PCT/FR2009/000124
§ 371 (c)(1),
(2), (4) Date: Nov. 15, 2010

(87) PCT Pub. No.: WO2009/109725
PCT Pub. Date: Sep. 11, 2009

(65) Prior Publication Data
US 2011/0048068 A1    Mar. 3, 2011

(30) Foreign Application Priority Data

Feb. 8, 2008  (FR) ..................................... 08 00669
Sep. 30, 2008  (FR) ..................................... 08 05367

(51) Int. Cl.
*B01D 53/22*    (2006.01)
(52) U.S. Cl. .................. 95/52; 95/43; 95/45; 96/4; 96/7; 96/9
(58) Field of Classification Search ................. 95/43, 45; 96/4, 7, 9
See application file for complete search history.

(56) References Cited

U.S. PATENT DOCUMENTS

| | | | |
|---|---|---|---|
| 3,604,246 A * | 9/1971 | Toren ................................ | 73/38 |
| 3,735,559 A | 5/1973 | Salemme | |
| 4,600,559 A | 7/1986 | Hiatt | |
| 4,612,019 A | 9/1986 | Langhorst | |
| 5,034,025 A * | 7/1991 | Overmann, III .................. | 95/52 |
| 6,171,374 B1 * | 1/2001 | Barton et al. ...................... | 96/7 |
| 7,311,760 B2 * | 12/2007 | Matsumura et al. ............... | 96/4 |
| 7,604,689 B2 * | 10/2009 | Siverklev .......................... | 96/4 |
| 8,157,891 B2 * | 4/2012 | Montie et al. ..................... | 95/43 |
| 2006/0021615 A1 | 2/2006 | Kertzman | |

FOREIGN PATENT DOCUMENTS

| WO | WO-9967621 A1 | 12/1999 |
|---|---|---|
| WO | WO-2006049434 A1 | 5/2006 |

* cited by examiner

*Primary Examiner* — Jason M Greene
*Assistant Examiner* — Anthony Shumate
(74) *Attorney, Agent, or Firm* — Connolly Bove Lodge & Hutz LLP

(57) ABSTRACT

The invention relates to a device for drying a gas, in particular air, that comprises at least one chamber (5) with an inlet (5*a*) for the flow of gas to be treated and an outlet (5*b*) for the flow of treated gas, said chamber being limited by at least one membrane (6) having a water vapor perviousness that is significantly higher than the perviousness to other gases or vapors, a humidity absorbing material being provided or flowing against the membrane (6) on the side opposite the chamber. The device includes a stack of plates (P1, P2) provided with central openings (A, B); each chamber (5) is formed by a central opening (A) located between two parallel membranes (6) while the humidity absorbing material is provided against each membrane (6); each plate (P1) is sandwiched between two plates (P2, P3) including a housing (B, B1) for the humidity absorbing material; and a plurality of chambers (5) are stacked and connected in series.

24 Claims, 4 Drawing Sheets

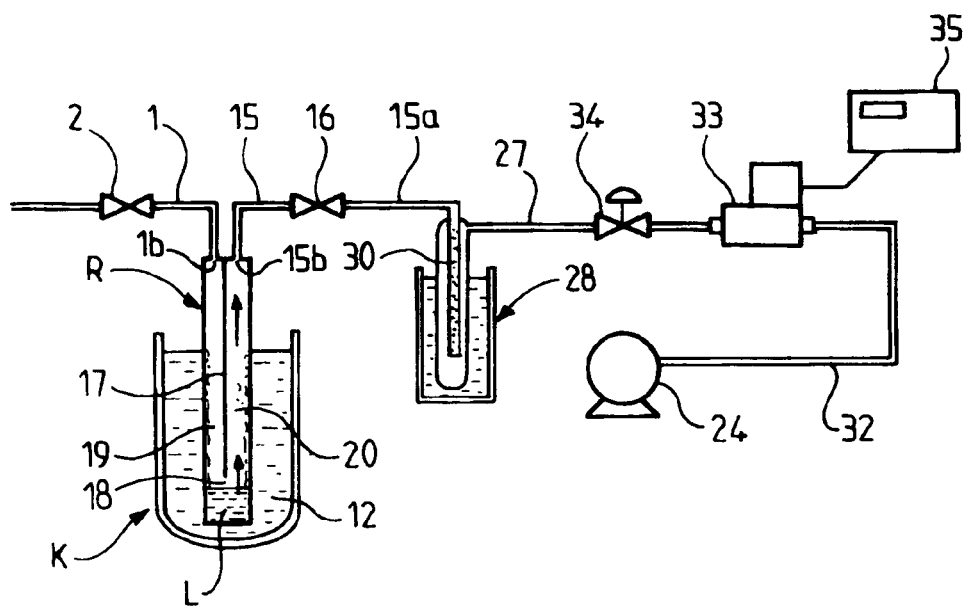
FIG.6
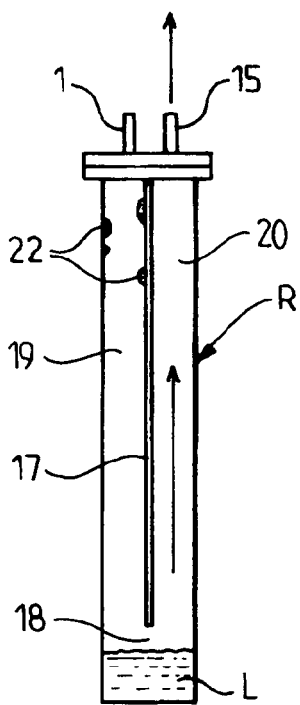 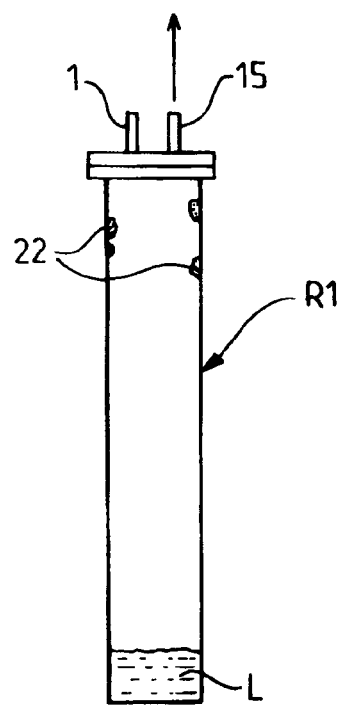
FIG.7  FIG.8

DEVICE FOR DRYING A GAS, IN PARTICULAR AIR, APPLICATION THEREOF TO A DEVICE, AND METHOD FOR COLLECTING A GAS SAMPLE

CROSS REFERENCE TO RELATED APPLICATIONS

This application is a National Phase filing under 35 U.S.C. §371 of PCT/FR2009/000124 filed on Feb. 4, 2009; and this application claims priority to Application No. 0800669 filed in France on Feb. 8, 2008; and Application No. 0805367 filed in France on Sep. 30, 2008 under 35 U.S.C. §119; the entire contents of all are hereby incorporated by reference.

The invention relates to a device for drying a gas, in particular air, which may contain various gaseous compounds, the drying having to make it possible to extract most of the water vapor present in the gas, without removing some of the other compounds present, or without modifying the content thereof.

The drying device in question is of the type of those which comprise at least one chamber, with an inlet for a gas flow to be treated and an outlet for the treated gas flow, this chamber being limited by at least one membrane, the water vapor permeability of which is substantially greater than its permeability with respect to other gases or vapors, a moisture-absorbing material being positioned, or circulating, against the membrane of the side opposite the chamber, the surface area of the chamber and of the membrane being determined, by taking into account the flow rate of gas and its assumed water vapor content, in order to ensure sufficient desiccation of the gas flow between the inlet and the outlet of the device.

US 2006/0021615 discloses a drying device of this type. It is desirable to improve the efficiency of such a device, and to facilitate its construction and its exploitation.

The invention relates more particularly to a device for drying air containing volatile organic compounds (VOCs) or odorous compounds that it is desired to analyze. More generally, the invention relates to any application for which it is necessary to have a moisture-free gas flow (chromatographic analyses, mass spectrometry, fuel cells, sampling of polar gases, etc.).

The analysis of gaseous compounds present in a main carrier gas, in particular air, generally requires processes which do not tolerate, or which poorly tolerate, a substantial presence of water vapor. This is the case, in particular, for gas chromatography, or for mass spectrometry.

Moreover, it is desirable for the drying device to allow a rapid and continuous treatment of the gas, under conditions that are simple to use.

The objective of the invention is therefore to provide a device for drying a gas which, while being of simple production, makes it possible to carry out a dynamic treatment, that is to say on a flow of gas, instead of a static treatment, while having a good efficiency and being of rapid implementation.

According to the invention, the device for drying a gas, in particular air, of the type defined previously, is characterized in that it comprises:
 a stack of plates provided with central openings, except for the outermost plates which are closed,
 each chamber is formed by a central opening provided in a plate, this central opening being between two parallel membranes, whilst the moisture-absorbing material is provided against the membranes on the side opposite the chamber, a gas inlet channel and an outlet channel passing through the wall of the plate which surrounds the central opening,
 each plate defining a chamber for the passage of the gas is sandwiched between two plates comprising a housing for the moisture-absorbing material,
 and several chambers are stacked, and connected, in series.

Advantageously, sealing means are provided between the various stacked plates.

The plates may be circular, crown-shaped or disk-shaped. Five chambers may be provided in series. The plates of the stack may be made of plastic, in particular made of polytetrafluoroethylene.

Preferably, the membrane is constituted by a polymeric membrane, in particular a membrane made of PET (polyethylene terephthalate), more particularly made of PET known under the trade name "Nalophan" which is supplied in the form of a film by KALLE GmbH (Germany).

The moisture-absorbing material may be formed by silica gel (SG). As a variant, the moisture-absorbing material comprises a circulating dry gas. Other moisture-absorbing materials may be used, especially zeolites.

Preferably, each plate defining a chamber for the passage of the gas is sandwiched between two plates that comprise a housing for the moisture-absorbing material.

Advantageously, the stack of plates is held together using clamping means, the plates comprising, on their periphery, radially protruding lugs through which holes pass, the stack being held using screws that pass through aligned holes. The lugs are offset angularly in order to make it possible to place the thickness of a nut between two plates, defining a chamber for the passage of the gas, separated by a plate comprising a housing for the moisture-absorbing material, or between two plates comprising a housing for the moisture-absorbing material separated by a plate defining a chamber for the passage of the gas.

The invention also relates to the application of the gas-drying device defined previously, to a device for collecting a sample of gas in an environment, in particular for an analysis of volatile organic compounds (VOCs) or of odors over a given time period, a device of the type of those which comprise a collection tube leading to a storage vessel for the sample, and a means for closing the vessel after collection.

The invention relates more particularly, but not exclusively, to such a collection device for carrying out measurements of VOCs or of odors in, or in the vicinity of, wastewater treatment plants, chemical factories, landfills, etc.

Conventionally, an occasional collection of gas at a given location is carried out in a bag, the volume of which may range from 20 to 60 liters. The sample thus collected constitutes an instantaneous "photo" of the surrounding air. This sample is then analyzed in a laboratory. The odors may be evaluated by olfactometry, with a jury of noses (operators qualified for assessing odors). Other types of analyses, for example by gas chromatography, are also possible.

The sample collected in a bag must not be kept for too long before the analysis since the products collected may evolve over time. Standards thus limit the time between the collection and the analysis, so that the distance between the analyzing laboratory and the collection site must not be too great so that the sample transport time remains shorter than the limit set.

Moreover, due to the limited volume of the collection bags, it is difficult to carry out a continuous collection of gas samples over a relatively long period.

Other sampling methods exist, which can be split into three groups:
 Sampling by adsorption onto an adsorbent bed (activated carbon, zeolite, Tenax, XAD, etc.); this method has the drawback of being selective, of being incompatible with certain compounds and of being unstable in the presence of moisture.

Sampling by storage in appropriate containers; the walls must be inert (Tedlar®, Nalophan, Teflon®, etc.).

Sampling by absorbent tubes; the compounds are retained on reactants, but these reactants are selective and the measurement may not be complete.

The objective of the invention is, above all, to ensure a continuous gas sample collection in an environment over a relatively long time while retaining the qualities of the sample, in a reduced volume. In particular, it is desirable to be able to carry out a continuous collection over several days, especially five to seven days. Moreover, it is desirable for the collection device to permit the transport of the sample from a distance without impairing its properties.

The application of the gas drying device, defined previously, to a device for collecting a sample of gas in an environment, in particular for an analysis of the VOCs or of the odors, over a given time period, is characterized in that:

the gas drying device is positioned in the collection tube, upstream of the storage vessel, and a storage vessel cooling means is provided in order to cool and maintain the vessel at a low enough temperature to condense, in liquid and/or solid form, at least the gaseous components to be analyzed in the sample.

The cooling means may be formed by a bath of liquefied gas, the boiling point of which at atmospheric pressure is at least below that of the gaseous components other than nitrogen and oxygen, the vessel being immersed in the bath of liquefied gas and constituting a condenser. The cooling means is advantageously formed by a bath of liquid nitrogen.

The condenser may be made of metal, especially made of stainless steel or of titanium, in a cylindrical form. The inner face of the wall of the condenser is advantageously coated with a protective layer constituted of a deposition of polytetrafluoroethylene (PTFE), or of a deposition of silane (SULFINERT/SILTEK from RESTEK).

The condenser may comprise an inner partition that extends along a diameter of the cross section of the condenser, the partition separating, in the upper portion, the inlet orifice and the outlet orifice, the lower edge of the partition being at a distance above the bottom of the condenser so that a lower passage exists between two chambers determined by the partition, the geometric axis of the condenser being vertical during the collection.

Preferably, a regulator of the flow rate of gas collected is positioned in the collection tube in order to keep the flow rate substantially constant throughout the collection time.

The collection device is provided in order to enable a continuous collection over a period which may range up to seven days.

The invention also relates to a process for the restitution of a gas sample collected by a device as defined previously, the VOCs or odor of which is to be analyzed, this process being characterized in that:

in the case of a sample collected in proximity to a VOC or odor emission source, the reconstitution is carried out by warming the sample to ambient temperature, the sample being restituted in its initial volume, or diluted in a larger volume, in the case of a sample collected at a distance from a VOC or odor emission source, the reconstitution comprises a step of concentrating the volatile compounds other than nitrogen and oxygen.

Advantageously, the step of concentrating volatile compounds other than nitrogen and oxygen comprises a vacuum distillation in order to evaporate the nitrogen and the oxygen. The volatile organic compounds possibly purged by the evaporated nitrogen and oxygen may be condensed in a cold trap.

The distillation may be carried out according to a technique based on pressure-expansion pulses, so that at each pulse, the condenser is pressurized with air or nitrogen, under a given pressure, which is optimal for the system, followed by a sudden expansion, via a drop in the pressure.

The vacuum distillation is stopped when the evaporated volume measured corresponds to almost all, in particular 99%, of the collected sample volume.

The invention consists, apart from the formats explained above, of a certain number of other formats, which will be mentioned more explicitly below as regards exemplary embodiments described with reference to the appended drawings, but which are in no way limiting. In these drawings:

FIG. 6 is a view that illustrates another variant of the restitution process;

FIG. 7 is a vertical schematic cross section with external parts of a condenser for the device according to the invention; and FIG. 8 shows, similarly to FIG. 7, one possible variant of the condenser.

Figure 1:
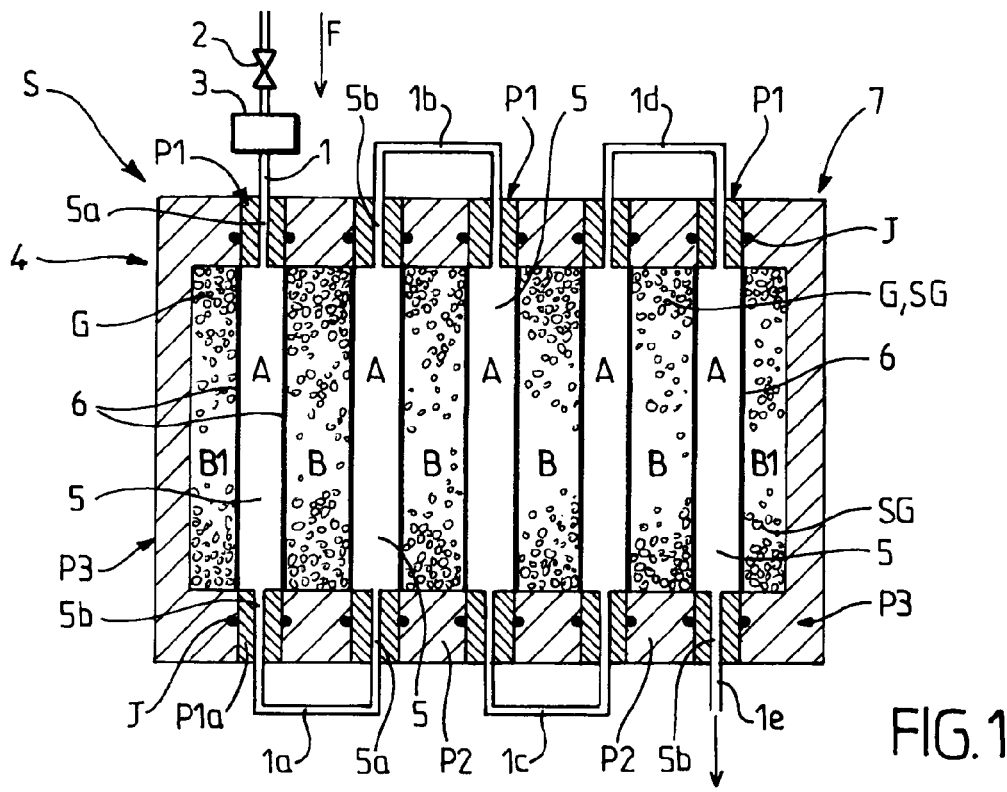
FIG. 1 is a cross-sectional diagram of a gas-drying device according to the invention.

By referring to FIG. 1 of the drawing, a device S can be seen for drying or desiccation of a gas constituted, in the example in question, by air loaded with volatile organic compounds, denoted in the abstract by VOCs, in gaseous form. The air, or more precisely the gaseous mixture of air and VOCs, is introduced into the device S by a tube 1, along a flow direction shown schematically by an arrow F. The terms "upstream" and "downstream" should be understood in accordance with this flow direction. A valve 2 is generally positioned in the tube 1 upstream of the device S and a filter 3 is generally provided in order to retain the solid particles optionally present in the gas to be analyzed.

The drying device S is formed by a desiccation means 4 positioned in the tube 1 downstream of the filter 3. This desiccation means 4 comprises one or more chambers 5, especially cylindrical chambers, connected in series by bends 1a, 1b, 1c, 1d of the tube.

The chambers 5 are formed by central openings A provided in parallel plates P1, the openings A emerging on each of the parallel faces of the plates P1. Each central opening A is surrounded by a peripheral wall P1a having a closed contour. An inlet channel 5a, having an axis parallel to the plane of the large open faces of the plate P1 passes through this contour P1a and, on the opposite side, an outlet channel 5b passes through the peripheral contour. The outlet channel 5b of the last plate P1 of the stack is connected to an outlet tube 1e. The cross section of the chambers 5 is greater than that of the tube 1.

At least one wall of the chamber 5, and preferably both walls parallel to the large faces of the plate P1, are formed by a polymer membrane 6, in particular that is made of PET (polyethylene terephthalate), more particularly that known under the trade name "Nalophan". The membrane 6 is generally constituted by a film having a thickness of the order of 20 μm. A layer G of moisture-absorbing material is positioned against the membrane 6 on the opposite side to the chamber 5. The layer G is advantageously formed of silica gel SG, for example in the form of granules. The water vapor concentration gradient is thus kept at a maximum on both sides of the membrane 6 in order to favor the permeation of the water vapor.

The layer G is advantageously housed in a chamber B formed by a central opening provided in a plate P2 having parallel faces, the opening emerging on each of the faces of the plate P2. The chamber B is thus surrounded by a closed peripheral contour P2a. Each chamber B is limited by two membranes 6 corresponding to two successive chambers 5.

A stack of plates P1, P2 is thus formed. The two end plates P3 are closed, but comprise a central cavity B1 facing the neighboring membrane 6, this cavity B1 being filled with moisture-absorbing material, especially silica gel SG (FIG. 2).

Figure 2:
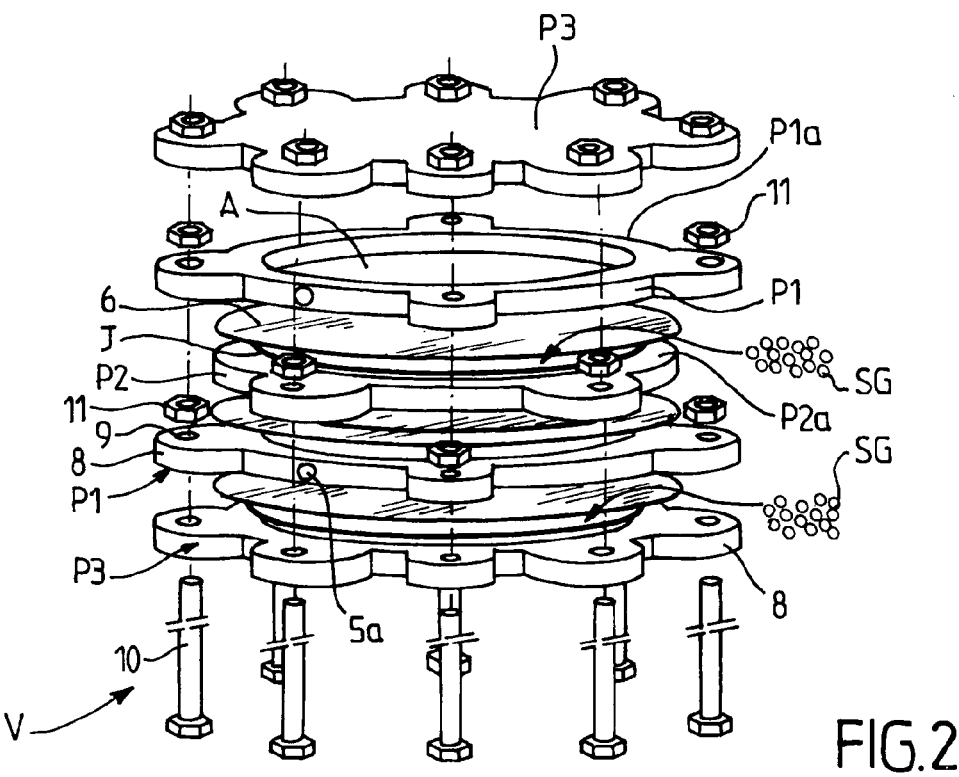
FIG. 2 is an exploded perspective view of an embodiment of the gas-drying device.

The stack, as can be seen in FIG. 2, may be held together using clamping means V. Seals J are provided between the successive plates of the stack in order to surround the chambers 5 in a leaktight manner. The plates P1, P2 and P3 are advantageously made from a plastic that is resistant to corrosive agents, in particular made of polytetrafluoroethylene (PTFE). The assembly of the plates forms an envelope 7.

According to the example of FIG. 1, five successive chambers 5 are provided in series, located in five plates P1, separated by four plates P2, with two end plates P3, i.e. in total eleven plates.

Advantageously, the plates have a circular shape and constitute crowns or disks as illustrated in FIG. 2. In this FIG. 2, only two plates P1, one plate P2 and the two end plates P3 have been represented. It should be understood that between the upper plate P1 of FIG. 2 and the upper plate P3, a succession of plates P2, P1 has not been represented for simplification.

According to the embodiment of FIG. 2, the circular plates comprise, at their periphery, radially protruding lugs 8 through which holes 9 pass. The stack is held together using clamping means V which comprise screws 10 that pass through aligned holes 9 and using nuts 11 provided on each plate for clamping to the preceding plate. The lugs 8 are angularly offset in order to make it possible to place the thickness of a nut 11 between two successive plates P1 separated by a plate P2, or between two plates P2 separated by a plate P1. Each plate, or disk, is clamped against the plate which is underneath using several screws. The central openings A are circular, and the seals J are O-rings.

The operation of the drying device S follows from the preceding explanations.

A flow of moist air is introduced by the tube 1, in order to travel through the successive chambers 5 in series and exit via the tube 1e as a flow of dry air suitable for being subjected to analyses.

The desiccation is carried out effectively, without altering the content of other gases, especially the VOC content of the air.

The device according to the invention enables the desiccation of a flow of moist air in order to prevent condensation of water and consequently losses of polar compounds, and makes it possible to avoid sensor failure.

The drying of the moist air flow is carried out under certain conditions by virtue of the phenomenon of permeation through polymer membranes, especially Nalophan membranes, without adversely affecting the other components present in the sample, the permeation kinetics of which are lower than those of the water vapor.

The device may be used for drying gas flows intended for various applications such as: chromatography, air samples, fuel cells. The invention makes it possible to dry a moist gas flow without adversely affecting the other components present in the flow, such as ammonia, benzene, toluene, methanol, etc.

The residence time of the sample inside the drying device must be long enough to enable the permeation of the water, and short enough to prevent the permeation of the other components.

The device must provide a sufficient surface area to allow the highest degree of mass transfer of water.

According to the experiments carried out in the laboratory, which made it possible to calculate the residence time and the water permeation rate, by means of the method of initial rates, and by taking into account that the air flow rate must be 15 ml/min, a typical microreactor design was proposed. The main parameters are given below:

| | |
|---|---|
| Surface area required | 2550 cm² |
| Internal volume (sum of the chambers A) | 900 cm³ |
| Geometry | cylindrical |
| Number of stages | 5 |
| Radius | 9.01 cm |
| Disk thickness | 0.71 cm |

The inlet 5a and outlet 5b orifices of the chambers 5 are, in particular, made of stainless steel, the surface area of which has been rendered inert with a suitable coating, especially a deposition of silane or of polysilane (Sulfinert/Siltek). The tubes 1a, . . . 1d, which connect the chambers in series, are especially made of polytetrafluoroethylene.

When the moist air flow passes through the chambers A, its moisture is removed and transferred to the chambers B by the phenomenon of permeation according to the following equation:

$$\frac{dn_A}{dA} = k\Delta C = k(C_w - C_{w0})$$

$$k = \frac{D_w}{\delta}$$

in which
$dn_A/dA$=variation of the water content per unit of time and of surface area (g/s·cm²)
k=a constant (cm/min) dependent on:
$D_w$=diffusivity (cm² per min)
δ=thickness of the boundary layer (cm)
$C_w$=concentration of the water vapor in the air (g/cm³)
$C_{wo}$=concentration of the water vapor in the environment of the chambers B (g/cm³)

$D_w$ depends on the temperature and δ depends on the gas flow rate. $C_{wo}$ is considered to be negligible since the chambers B are filled with silica gel which is a powerful water absorber so that the difference between $C_w$ and $C_{wo}$ may be considered to be maximum all the time.

Using the drying device of the invention, around 90-95% moisture removal may be achieved in a dynamic air flow under difficult environmental moisture conditions (40-45° C. and 100% relative humidity).

The drying or desiccation device according to the invention may be used in a device for collecting gas samples such as that described with respect to the following figures. This drying device may of course be used for other applications.

Figure 3:
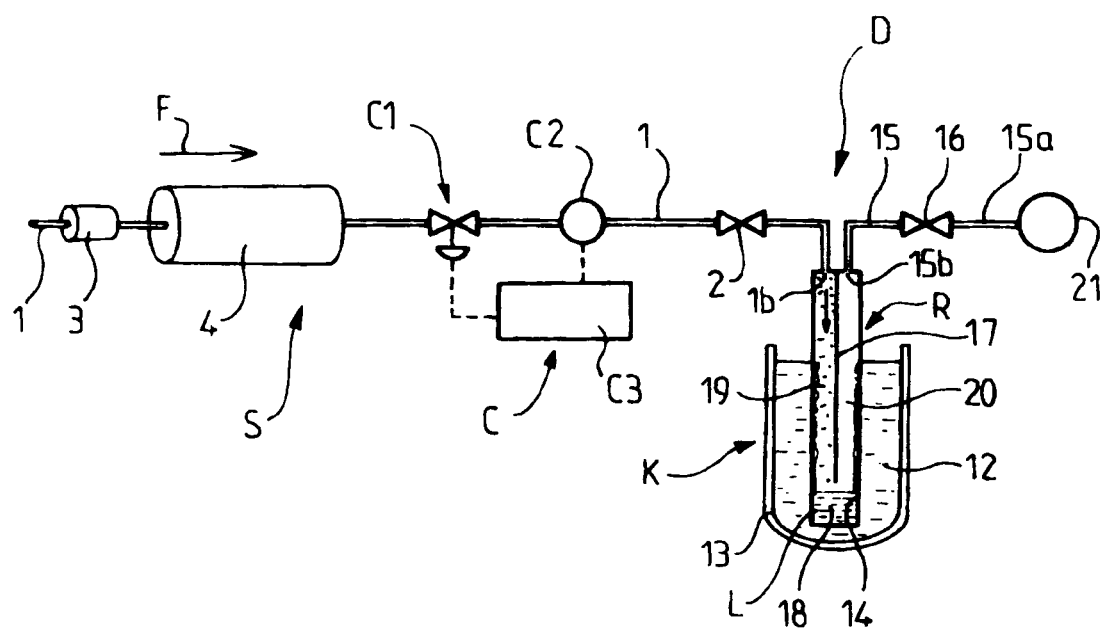
FIG. 3 is a diagram of a gas sample collection device according to the invention.

FIG. 3 illustrates the application of the drying device S to a device D for collecting a sample of gas in an environment, in particular in the atmosphere. The collection tube 1 leads to a storage vessel R for the sample. A valve 2, positioned in the tube 1 upstream of the vessel R, constitutes a means of closing the vessel R after a collection.

In the upstream portion of the tube 1, the filter 3 is positioned in order to retain solid particles optionally present in the gas sample to be collected. This filter 3 may be provided in order to retain particles having a dimension which is greater than or equal to 7 μm (seven micrometers).

The desiccation means 4, which is positioned in the tube 1 downstream of the filter 3 and upstream of the vessel R, makes it possible to remove moisture from the sample, without adversely affecting the other components of this sample, even the polar components.

A regulator C of the flow rate of gas collected is positioned in the tube 1 downstream of the desiccation means 4. The regulator C comprises an adjustable flow rate valve C1, a flow meter C2 installed in the tube 1 downstream of the valve C1, and a control unit C3 connected to the flow meter C2 in order to recover therefrom information on the flow rate. The control unit C3 compares the flow rate measured with a setpoint value entered into the unit C3 and controls, via an appropriate connection, the valve C1 in order to maintain the flow rate at the desired value.

The valve 2 is installed in the tube 1 downstream of the flow meter C2. The tube 1 extends downstream of the valve 2 in order to open, via an inlet orifice 1b, into the vessel R.

A cooling means K is provided in order to cool the storage vessel R to a low enough temperature in order to condense, in liquid or solid form, at least the gaseous components, especially the VOCs (volatile organic compounds), other than nitrogen and oxygen, to be analyzed in the sample.

Advantageously, the cooling means K is constituted by a bath 12 of liquid nitrogen contained in a thermally insulating flask, especially a Dewar flask 13. The vessel R is immersed in the bath 12 and will be denoted hereinbelow by the term "condenser". The condenser R is sunk into the bath 12 to a depth at least equal to half its height. The flask 13 has been illustrated schematically and the means for holding the condenser R relative to the flask 13 are not represented. However, the assembly is produced in a unit which may be moved and transported without risk of spilling the liquid nitrogen.

The condenser R may be of cylindrical shape having an axis parallel to the geometric axis of the flask 13. By way of indication and non-limitingly, the outer diameter of the condenser R may be of the order of 5 cm, and its height of the order of 50 cm. During the collection, the geometric axis of the condenser R is vertical.

The condenser R is made of metal, especially of stainless steel or of titanium to prevent reactions with the gas collected that are capable of impairing the sample. In order to further reduce the risk of reaction, it is advantageous to coat the inner face 14 of the wall of the condenser R with a protective layer, especially a deposition of polytetrafluoroethylene (PTFE), or a deposition of silane or of polysilane (SULFINERT/SILTEK).

A second tube 15 leads from an outlet orifice 15b, at the top of the condenser R, in order to allow the collection of the sample to be analyzed. A valve 16 is placed in the tube 15 which extends via a branch 15a downstream of the valve 16.

It has been observed that the VOCs (volatile organic compounds) have a tendency to condense in solid form, for example as scale or as droplets 22 (FIGS. 7 and 8) in the upper part of the condenser. On the contrary, nitrogen and oxygen condense in the liquid phase L and fall into the bottom of the condenser.

Advantageously, the condenser R comprises an internal partition 17 that extends along a diameter of the cross section of the tube. The partition 17 separates, in the upper part, the orifices 1b, 15b. The lower edge of the partition 17 is at a distance above the bottom of the condenser R so that a lower passage 18 exists between the two chambers 19, 20, of semicircular cross section, determined by the partition 17. The chamber 19 in which the sample arrives and condenses is separated from the chamber 20 through which the sample is evacuated, so that the risk of entraining VOCs condensed by the gaseous nitrogen or oxygen is reduced.

The collection of a gas sample is carried out in the following manner.

The collection device D is installed on the site where the collection must take place. The two valves 2, 16 are closed.

Before the actual collection, the condenser R may be put under vacuum. Such an initial step of putting under vacuum makes it possible, on the one hand, to evacuate the air from the condenser R which could slightly modify the composition of the sample collected and, on the other hand, to facilitate the start of the collection. For this initial operation of putting under vacuum, the branch 15a is connected to a vacuum pump 21 and the valve 16 is open whereas the valve 2 remains closed. When a sufficient degree of vacuum has been obtained in the condenser R, the valve 16 is closed again and the vacuum pump 21 is stopped and separated from the branch 15a.

The inlet flow rate desired for the gas is displayed in the control unit C3 and the actual collection then begins by opening the valve 2.

The condenser R is at reduced pressure due to the fact that it is kept at low temperature, namely the liquefaction temperature of nitrogen under atmospheric pressure, i.e. −196° C. This reduced pressure is accentuated if an initial step of putting under vacuum was carried out. A flow of gas from the atmosphere passes, via natural suction, through the tube 1 and travels towards the condenser R where it is condensed.

The nitrogen and oxygen from the air condense in liquid form L on the lower part of the condenser R so that a reduced pressure is maintained in the condenser. The other gaseous components collected condense in liquid form or in the form of solid blocks such as 22 (FIG. 7) against the walls of the condenser R. This is the case, in particular, for certain volatile organic compounds (VOCs) that are sources of odors.

The condensation of the collected sample makes it possible to store, in a reduced volume, a large sample of gas.

At the start of the collection, the reduced pressure is relatively high in the condenser R and the suction is strong, so that the adjustable valve C1 is placed, by the unit C3, in a position of maximum throttling in order to curb the suction and establish the flow rate at the desired value. As the condenser R fills with liquid and as the suction becomes less strong, the control unit C3 gradually controls the opening of the valve C1. At the end of the collection, the valve 2 is closed, the valve 16 remaining closed.

The device D of the invention makes it possible to collect, at a site, a gaseous sample continuously over several days, especially five to seven days, with a constant collection flow rate. The sample then represents an exact average of the events which took place during the collection time. Of course, the device D allows collections over a shorter time, for example one day or several hours.

The condensation of the gases collected makes it possible to store the sample while avoiding reactions capable of adversely affecting the composition of the sample between the time of collection and the time of analysis.

The gas sample thus collected is stored under cryogenic conditions, which ensures its stability and enables transport of long duration. It is thus possible to collect samples at locations far from the analysis laboratory without risk of degradation and/or reaction of the compounds of the sample.

In order to reconstitute the sample, without adversely affecting its components, in view of an analysis by olfactometry and/or by gas chromatography, or by any other analytical method, the following procedure is used.

The unit of measurement is the European odor unit per cubic meter $OU_E/m^3$. The odor concentration is measured by determining the dilution factor required to reach the detection threshold. The odor concentration at the detection threshold is, by definition, 1 $OU_E/m^3$. The odor concentration is then expressed in terms of multiples of the detection threshold. The measurement range is generally from $10^1$ $OU_E/m^3$ to $10^7$ $OU_E/m^3$ (including the predilution).

Two cases are to be envisioned, in particular for the sample collections in view of analyzing the VOCs or the odors.

First Case

The sample was collected near to an odor emission source and, consequently, the odor concentration of the sample is assumed to be high, in particular greater than 100 $OU_E/m^3$. Under such conditions, it is not necessary to concentrate the gases during the reconstitution in order to be able to carry out the analysis.

Figure 4:
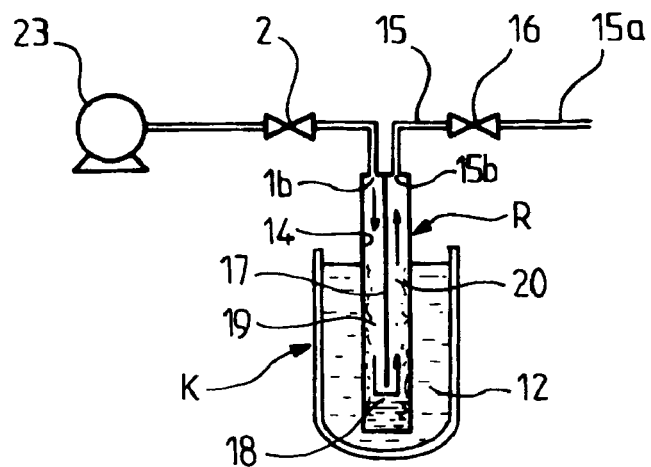
FIG. 4 is a diagram of the process for restitution of a collected gas sample.

The reconstitution may then be carried out by warming the sample, in the condenser R, by purging with air or nitrogen at ambient temperature as illustrated in FIG. 4. In order to do this, an air pump 23 is connected to the tube 1 upstream of the valve 2. The valves 2 and 16 are opened and a bag or similar container (not represented) is connected to the tube 15a in order to recover the gas collected and the purging air. The sample is then reconstituted in a volume greater than the initial volume, which corresponds to a dilution of the sample in the inert purging gas.

As a variant, instead of purging the condenser R with a gas, this condenser R is warmed, for example to ambient temperature, the valve 2 is kept closed and the valve 16 is opened, the gas collected being recovered at the outlet of the tube 15a. The warming may be obtained by partly or completely removing the condenser R from the bath 12.

Second Case

The sample was collected in the surroundings, at a distance from an emission source and the odor concentration of the sample is assumed to be less than 30 $OU_E/m^3$.

When the sample collected has a relatively low concentration of VOCs or odors, in order to carry out the measurement it is desirable to concentrate the volatile organic compounds of the sample which are the source of the odors.

Figure 5:
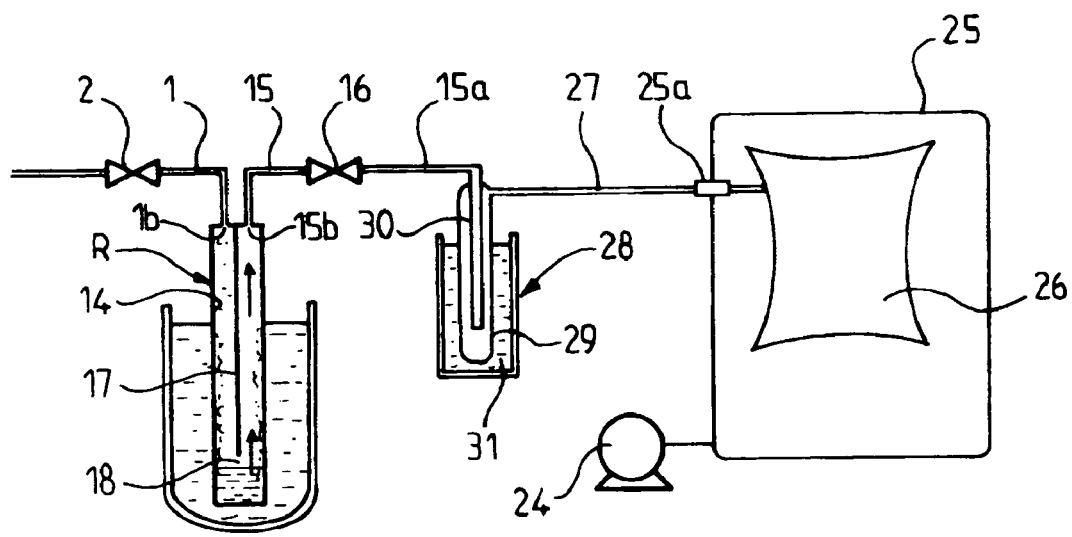
FIG. 5 is a diagram that illustrates one variant of the restitution process of FIG. 4.

A vacuum distillation of the sample is then carried out, as illustrated in FIG. 5.

Without removing the condenser 2 from the bath of liquid nitrogen, the most volatile compounds of the sample, namely nitrogen and oxygen, are evaporated under the effect of a vacuum created by a vacuum pump 24. The pump 24 is connected to a rigid-walled vacuum chamber 25 in which a bag 26 made of a flexible material, for example made of PET polymeric membrane such as those known under trade names "Nalophan" or made of PVF (polyvinyl fluoride) such as those known under the trade names "Tedlar®", is placed. The bag 26 is connected to a tube 27 which passes, in a leaktight manner, through the wall of the chamber 25 via a coupling 25a. The tube 27, at its end far away from the bag 26, is coupled to the outlet of a cold trap 28. The cold trap 28 comprises a cylindrical envelope 29, the upper end of which is connected to the tube 27. This envelope 29 is sealed at its lower end and is passed through in a leaktight manner, at its upper end, by a vertical dip tube 30 coupled to the branch 15a. The dip tube 30 stops at a distance from the bottom of the envelope 29, which is immersed in a cooling bath 31, in particular a bath of liquid nitrogen.

The reconstitution of the sample by vacuum distillation, with concentration of the volatile organic compounds, is carried out as follows.

At the start of the operation, the valves 2 and 16 are closed. The vacuum pump 24 is started in order to create a sufficient vacuum in the chamber 25.

The valve 16 is then opened, and the sample that is in the condenser R is exposed to a relative vacuum which gives rise to the evaporation of the nitrogen and of the oxygen of the sample. The other volatile organic compounds of the sample, the liquefaction temperature of which is greater than that of nitrogen and of oxygen, remain in condensed form.

However, a fraction of these VOCs may be entrained by the nitrogen and/or the oxygen which evaporates. This fraction of VOCs will then be condensed in the cold trap 28.

After extraction of the nitrogen and of the oxygen from the sample, the latter is concentrated in VOCs and may be restituted by purging with a gas at ambient temperature or by warming the condenser R and the tube 30 by removing them from their cooling bath.

The distillation may be carried out according to a pseudo-flash technique based on pressure-expansion pulses, so that at each pulse, the condenser R is pressurized with air or nitrogen, under a given pressure, which is optimal for the system, followed by a sudden expansion, via a drop in the pressure. It is thus possible to carry out a very high restitution of the VOCs.

In order to determine the moment when the distillation should be stopped, when the nitrogen and oxygen have been removed for the most part from the sample, several routes are open as explained below.

A first route consists in going on the oxygen content of the gas flow originating from the sample. This method can only be carried out during sequential operations due to the limits of the measurement devices. Due to the fact that oxygen (liquefaction temperature: −183° C. under atmospheric pressure) is less volatile than nitrogen (liquefaction temperature: −196° C. under atmospheric pressure), the more the vacuum distillation progresses, the more the exiting gas flow is enriched with oxygen. The stopping of the distillation is ordered when the oxygen content of the exiting flow is greater than a given value, in particular 30% by volume.

A second route consists in measuring the degree of vacuum, which increases rapidly when the evaporation of the nitrogen and of the oxygen from the sample is finished. A device (not represented) for measuring the reduced pressure is installed downstream of the cold trap and upstream of the vacuum pump. The stopping of the distillation is ordered when a rapid increase in the reduced pressure is detected.

A third preferred route consists in measuring the volume of gases evaporated. The volume of the sample collected, under atmospheric pressure and at ambient temperature, is known. The sample is composed of almost 100% nitrogen and oxygen. When the evaporated volume measured corresponds to almost all of the sample, in particular to 99% of the volume of the sample, the distillation is stopped.

FIG. 6 illustrates an implementation of the third route. The vacuum pump 24 is connected via a tube 32 to a flow meter 33, which is connected upstream to the outlet tube 27 of the cold trap 28 via an adjustable throttling valve 34. A control and adding unit 35 receives information from the flow meter 33.

The operation for recovering the condensed sample by a vacuum distillation, according to FIG. 6, takes place under conditions similar to those described with respect to FIG. 5, the unit 35 making it possible to determine the volume of gas evaporated, and to stop the distillation when the limit set is reached.

FIG. 8 is a diagram of one possible embodiment variant of a condenser R1 formed by a cylindrical envelope that does not comprise the diametral partition 17 from FIG. 7. The condenser R1 has the following drawback. The solid blocks or scale 22 of volatile organic compounds may form on the inner surface of the wall of the container R1 on the outlet side of this container. When the nitrogen and oxygen are extracted, especially by vacuum distillation, the purging carried out by the gases against the blocks 22 entrains a fraction of the VOCs, so that the composition of the sample which will then be reconstituted is altered thereby.

Such a drawback does not occur with a condenser R such as that from FIG. 7, but the solution of FIG. 8 remains acceptable.

Regardless of the variant adopted, the solution of the invention makes it possible to collect a sample of gas over a given period which may range from a few hours up to seven days, continuously, in a reduced volume. The transport and reconstitution of the sample may take place without altering the initial composition of the sample, especially when it is a question of analyzing the odors of the sample.

The invention is not limited to the analysis of odors and may be applied to any gas sample collection.

The invention claimed is:

1. A device for drying a gas, in particular air, which may contain various gaseous compounds, the drying having to make it possible to extract most of the water vapor present in the gas, without removing some of the other compounds present, or without modifying the content thereof, comprising at least one chamber, with an inlet for a gas flow to be treated and an outlet for the treated gas flow, this chamber being limited by at least one membrane, the water vapor permeability of which is substantially greater than its permeability with respect to other gases or vapors, a moisture-absorbing material being positioned, or circulating, against the membrane on the side opposite the chamber, the surface area of the chamber and of the membrane being determined, by taking into account the flow rate of gas and its assumed water vapor content, in order to ensure sufficient desiccation of the gas flow between the inlet and the outlet of the device, wherein it comprises:
   a stack of plates provided with central openings, except for the outermost plates which are closed,
   each chamber is formed by a central opening provided in a plate, this central opening being between two parallel membranes, whilst the moisture-absorbing material is provided against the membranes on the side opposite the chamber, a gas inlet channel and an outlet channel passing through the wall of the plate which surrounds the central opening,
   each plate defining a chamber for the passage of the gas is sandwiched between two plates comprising a housing for the moisture-absorbing material,
   and several chambers are stacked, and connected, in series.

2. The device as claimed in claim 1, characterized in that sealing means are provided between the various stacked plates.

3. The device as claimed in claim 1, wherein in that the plates are circular, crown-shaped or disk-shaped.

4. The device as claimed in claim 1, wherein five chambers are provided in series.

5. The device as claimed in claim 1, wherein the plates of the stack are made of plastic, in particular of polytetrafluoroethylene.

6. The device as claimed in claim 1, wherein the membrane is constituted by a polymer membrane, in particular a PET (polyethylene terephthalate) membrane.

7. The device as claimed in claim 6, wherein the membrane is constituted by a membrane made of PET known under the trade name "Nalophan".

8. The device as claimed in claim 1, wherein the moisture-absorbing material is formed by silica gel (SG).

9. The device as claimed in claim 1, wherein the moisture-absorbing material comprises a circulating dry gas.

10. The device as claimed in claim 1, wherein the stack of plates is held together using clamping means, the plates comprising, on their periphery, radially protruding lugs through which holes pass, the stack being held using screws that pass through the aligned holes.

11. The device as claimed in claim 10, wherein the lugs are angularly offset in order to make it possible to place the thickness of a nut between two plates, defining a chamber for the passage of the gas, separated by a plate comprising a housing for the moisture-absorbing material, or between two plates comprising a housing for the moisture-absorbing material separated by a plate defining a chamber for the passage of the gas.

12. An application of a device for drying a gas, in particular air, as claimed in claim 1, to a device for collecting a sample of gas in an environment, in particular for an analysis of the VOCs or of the odors, over a given time period, wherein:
   the gas drying device is positioned in the collection tube, upstream of the storage vessel,
   and a storage vessel cooling means is provided in order to cool and maintain the vessel at a low enough temperature to condense, in liquid and/or solid form, at least the gaseous components to be analyzed in the sample, the vessel constituting a condenser.

13. The application as claimed in claim 12, wherein the cooling means is formed by a bath of liquid nitrogen, the condenser being immersed in the bath.

14. The application as claimed in claim 12, wherein the condenser is made from metal in a cylindrical form.

15. The application as claimed in claim 14, wherein the condenser is made of stainless steel or of titanium.

16. The application as claimed in claim 14, wherein the inner face of the wall of the condenser is coated with a protective layer constituted of a deposition of polytetrafluoroethylene (PTFE), or of a deposition of silane (SULFINERT/SILTEK).

17. The application as claimed in claim 12, wherein the condenser comprises an inner partition that extends along a diameter of the cross section of the condenser, the partition separating, in the upper portion, the inlet orifice and the outlet orifice, the lower edge of the partition being at a distance above the bottom of the condenser so that a lower passage exists between two chambers determined by the partition, the geometric axis of the condenser being vertical during the collection.

18. The application as claimed in claim 12, wherein a regulator of the flow rate of gas collected is positioned in the collection tube in order to keep the flow rate substantially constant throughout the collection time.

19. The application as claimed in claim 18, wherein the regulator comprises an adjustable flow rate valve, a flow meter installed in the tube downstream of the valve, and a control unit connected to the flow meter in order to recover information on the flow rate therefrom, the control unit controlling, via a suitable connection, the valve in order to keep the flow rate at the desired value, the device being provided in order to enable a continuous collection over a period which may range up to seven days.

20. A process for the restitution of a gas sample collected as claimed in claim 12, the odor of which is to be analyzed, wherein:

in the case of a sample collected in proximity to an odor emission source, the reconstitution is carried out by warming the sample to ambient temperature, the sample being restituted in its initial volume, or diluted in a larger volume, in the case of a sample collected at a distance from an odor emission source, the reconstitution comprises a step of concentrating the volatile compounds other than nitrogen and oxygen.

21. The process as claimed in claim 20, wherein, in the case of a sample collected at a distance from an odor emission source, the step of concentrating volatile compounds other than nitrogen and oxygen comprises a vacuum distillation in order to evaporate the nitrogen and the oxygen.

22. The process as claimed in claim 21, wherein the volatile organic compounds possibly purged by the evaporated nitrogen and oxygen are condensed in a cold trap.

23. The process as claimed in claim 21, wherein the distillation is carried out according to a technique based on pressure-expansion pulses, so that at each pulse, the condenser is pressurized with air or nitrogen, under a given pressure, which is optimal for the system, followed by a sudden expansion, via a drop in the pressure.

24. The process as claimed in claim 21, wherein the vacuum distillation is stopped when the evaporated volume measured corresponds to almost all, in particular 99%, of the collected sample volume.

* * * * *